(12) United States Patent
Liu et al.

(10) Patent No.: US 8,551,541 B2
(45) Date of Patent: Oct. 8, 2013

(54) DISINFECTANT MAKING AIR FRESH AND PREPARATION AND METHOD AND USE THEREOF

(75) Inventors: Liang Liu, Hong Kong (CN); Hua Zhou, Hong Kong (CN)

(73) Assignee: Everite Consultants Ltd., Kowloon (HK)

( * ) Notice: Subject to any disclaimer, the term of this patent is extended or adjusted under 35 U.S.C. 154(b) by 0 days.

(21) Appl. No.: 13/202,454

(22) PCT Filed: Feb. 20, 2009

(86) PCT No.: PCT/CN2009/000168
§ 371 (c)(1),
(2), (4) Date: Aug. 19, 2011

(87) PCT Pub. No.: WO2010/094151
PCT Pub. Date: Aug. 26, 2010

(65) Prior Publication Data
US 2011/0300243 A1    Dec. 8, 2011

(51) Int. Cl.
*A61K 36/61* (2006.01)
*A61K 36/54* (2006.01)
*A61K 36/00* (2006.01)

(52) U.S. Cl.
USPC .......................... 424/742; 424/739; 424/725

(58) Field of Classification Search
None
See application file for complete search history.

(56) References Cited

U.S. PATENT DOCUMENTS

2010/0015115 A1    1/2010    Yie et al.

FOREIGN PATENT DOCUMENTS

| CN | 1128672 A | 8/1996 |
|---|---|---|
| CN | 1156540 A | 8/1997 |
| CN | 1927383 | 3/2007 |
| CN | 101336646 | 1/2009 |
| CN | 101455850 A | 6/2009 |
| WO | WO98/40086 | 9/1998 |

OTHER PUBLICATIONS

Bure et al. (2004) J. Essent. Oil Res., 16, pp. 17-19.*
Cermelli et al.(2008) Curr. Microbiol. 56: pp. 89-92.*
Chaieb et al. (2007) Phytother. Res. 21, pp. 501-506.*
Web article entitled "Mentha and Schizonepeta" by Subhuti Sharmananda (available at http://www.itmonline.org/arts/metha.htm). Downloaded from website Oct. 4, 2012.*
Website document entitled: "Hwaairfan's Blog: *Forsythia* (Orchid) Oil". Available at http://hwaairfan.wordpress.com/it-makes-good-scents/fennel-oil/forsythia-orchid-oil. Downloaded from website Oct. 4, 2012.*
Park et al. (2006) J. Econ. Entomol. 99(5): pp. 1717-1721.*
Chaieb et al. (2007) Micoses 50, pp. 403-406.*
Cuellar et al. (1998) Phytotherapy Research, vol. 12, 18-23.*
Ozaki et al. (2000) Biol. Pharm. Bull. 23(3): 365-367.*
Jiao et al. (2012) Food Chemistry 134: 235-243.*
Ni et al. (2009) Journal of Ethnopharmacology 124: 79-86.*
Zhai et al. (2010) Chin. J. Chem. 28, 2513-2519.*
Jie et al. (2001) J. Norwest Normal University (Natural Science) 37(4): 77-81.*
Marion et al. (1994) J. Essenti. Oil Res. 6, pp. 379-387.*
PCT International Search Report and Written Opinion for PCT International Application No. PCT/CN2009/000168 completed Nov. 13, 2009.
Supplementary European Search Report for European Patent Application No. EP09840202, completed Jan. 21, 2013.

* cited by examiner

*Primary Examiner* — Chris R Tate
*Assistant Examiner* — Russell Fiebig
(74) *Attorney, Agent, or Firm* — Barnes & Thornburg LLP (57) ABSTRACT

The air-refreshing disinfectants currently sold in the market mostly contain artificially synthesized chemical disinfectants. Frequent exposure to the air containing such chemicals may be somewhat harmful to the human body. Therefore the present invention provides an air-refreshing disinfectant, and in particular an air-refreshing disinfectant which is not chemically synthesized and takes natural materials as raw materials and traditional Chinese medicinal volatile oils as main effective ingredients. It is characterized by bacteriostatic and antiviral effects, long-lasting fragrance and cost-effectiveness, and is beneficial to human health. To achieve this objective, the present invention, by taking advantage of the bacteriostatic, antiviral and fragrant characteristics of traditional Chinese medicinal volatile oils, employs specific combinations of eucalyptus oil, clove oil, patchouli oil, forsythia oil and schizonepeta oil as the active ingredients of the air-refreshing disinfectant.

25 Claims, 1 Drawing Sheet

DISINFECTANT MAKING AIR FRESH AND PREPARATION AND METHOD AND USE THEREOF

CROSS-REFERENCE TO RELATED APPLICATIONS

This application is a U.S. national counterpart application of PCT International Application Serial No. PCT/CN2009/000168 filed Feb. 20, 2009. The disclosure of PCT/CN2009/000168 is hereby incorporated herein by reference.

TECHNICAL FIELD

The present invention relates to an air-refreshing disinfectant, in particular to an air-refreshing disinfectant which is not chemically synthesized and which takes natural materials as raw materials and traditional Chinese medicinal volatile oils as main effective ingredients.

BACKGROUND ART

With the growing deterioration of the environment and the increasing accumulation of harmful substances in the air, peculiar smells and air infection affect the mood, health and working efficiency of the people. Cold, influenza and upper respiratory tract infection are the common and frequently-occurring diseases in the winter and spring seasons. They are mainly spread by spittles and airborne cross infection, and the incidences are especially high in places with a crowd of people and poor ventilation, such as hospitals, schools, and offices, etc. This is mainly because there are various pathogenic microorganisms present in the air in those places, such as influenza virus, rhinovirus, respiratory syncytial virus, adenovirus, *Streptococcus haemolyticus*, staphylococci, *E. coli* and the like. Therefore, disinfection of the air constitutes an important means to prevent and control such cross-infection. Nowadays, air-refreshing disinfectants are generally sprayed in the air in homes, hospitals, hotels, restaurants and other public places in order to kill the harmful microorganisms and remove peculiar smells in the air. However, the air-refreshing disinfectants currently sold in the market mostly contain synthetic chemical disinfectants. Frequent exposure to the air with such chemicals may be somewhat harmful to the human body. Therefore, it is very important to develop a safe, effective and natural air-refreshing disinfectant for cleansing indoor air.

SUMMARY OF THE INVENTION

With regard to the disadvantages of the air refreshing disinfectants of the prior art, the present invention discloses an air-refreshing disinfectant comprising traditional Chinese medicinal volatile oils as main effective ingredients, which is characterized by bacteriostatic and antiviral effects, long-lasting fragrance and cost-effectiveness, and is beneficial to human health.

In order to screen for formulations having a notable effect, three microbial strains *Staphylococcus aureus, Staphylococcus albus* and *E. coli*, and influenza A virus FM1 strain were chosen to evaluate the bacteriostatic and antiviral effects of the disinfectant product of the present invention. Among common pathogenic bacteria and viruses, staphylococci, enteric bacilli and influenza viruses are bacteria or viruses having important medical implications. These bacteria or viruses are widely present in nature, such as in air, soil, water or on articles, and also reside on the skin of humans and animals and in their cavities and tracts communicating with the outside. The carrier rate of pathogenic staphylococci in general population is 20% to 50%, while that in medical personnel is up to 70%. *Staphylococcus albus* and *E. coli* are two of the six main bacteria causing nosocomial infection, the infection rate of *E. coli* being the highest. *Technical Standard For Disinfection* (2002 Edition) issued by the Ministry of Public Health of China clearly states that the microorganisms used in an assay on the microbicidal effect of disinfectants include *Staphylococcus aureus, Staphylococcus albus* and *E. coli*, among others, and the microorganism used in an assay for the appraisal of air disinfection effect is *Staphylococcus albus*. Additionally, among the influenza A, B and C viruses, influenza A virus is most prevalent. Therefore, in the present invention, the three microbial strains *Staphylococcus aureus, Staphylococcus albus* and *E. coli*, and influenza A virus FM1 strain representative of pathogenic organisms were chosen for use in the appraisal of bacteriostatic and antiviral effects in the Examples hereinafter, and the results obtained can reflect the actual conditions and practical value of the disinfectant product of the present invention with regards to air disinfection and refreshing.

As described above, with regard to the disadvantages of the air-refreshing disinfectants of the prior art, the present invention discloses an air-refreshing disinfectant comprising traditional Chinese medicinal volatile oils as main effective ingredients, which is characterized by bacteriostatic and antiviral effects, long-lasting fragrance and cost-effectiveness, and is beneficial to human health.

To achieve this objective, the present invention provides specific combinations of eucalyptus oil, clove oil, patchouli oil, forsythia oil and schizonepeta oil as the active ingredients of the air-refreshing disinfectant.

The compositions of the present invention described above optionally comprise a vehicle. Where a vehicle is present, the ratio of the vehicle and the volatile oils can vary in a relatively wide range without affecting the effect.

There is no particular limitation on the vehicle that is useful, so long it serves to achieve the objective of the present invention.

The above-said air-refreshing disinfectant can be dissipated into the air by means of heating or spraying, among others, or can be used to filter and cleanse the air, so as to achieve the objective of refreshing and disinfecting the air.

In comparison with the prior art, the present invention has the following advantages:

1. The disinfectant has bacteriostatic and antiviral effects, has a fragrant scent, can refresh the air and remove peculiar smells, and can bring the users a refreshing, comfortable and sobering feeling. It can be used in a broad variety of places such as homes, offices, business locales, hotels, and carriages, etc, especially in hospitals, greatly reducing chances of infection in addition to making people sober and comfortable.

2. The product is stable and durable, low in price and readily acceptable to the consumers.

3. The production process of the product is simple, mature and easy to operate, and requires low investment in equipments and manufacture.

4. The formulation is comprised of traditional Chinese medicinal volatile oils and thus the product is safe and reliable.

In particular, the present invention provides the following technical solutions:

1. A formulation comprising compounded volatile oils, said volatile oils being eucalyptus oil, forsythia oil, clove oil, patchouli oil and schizonepeta oil.

2. The formulation according to technical solution 1, which is an air-refreshing disinfectant formulation.

3. The formulation according to technical solution 1 or 2, wherein said formulation further comprises a vehicle.

4. The formulation according to technical solution 1 or 2, wherein said formulation is comprised of eucalyptus oil, forsythia oil, clove oil, patchouli oil and schizonepeta oil.

5. The formulation according to any one of technical solutions 1-4, wherein said eucalyptus oil is the volatile oil extracted from bluegum—*Eucalyptus globulus* Labill of the Myrtaceae family, or camphor tree—*Cinnamomum camphora* (L.) Presl of the Lauraceae family, or other plants of the same genera to which the above two plants belong in the above two families.

6. The formulation according to any one of technical solutions 1-5, wherein said forsythia oil is the volatile oil extracted from the dried fruits of weeping forsythia—*Forsythia suspensa* (Thunb.) Vahl of the Oleaceae family.

7. The formulation according to any one of technical solutions 1-6, wherein said clove oil is the volatile oil extracted from the dried flower buds of clove—*Eugenia caryophyllata* Thunb. of the Myrtaceae family.

8. The formulation according to any one of technical solutions 1-7, wherein said patchouli oil is the volatile oil extracted from the dried stems and leaves of patchouli—*Pogostemon cablin* (Blanco) Benth of the Lamiaceae family.

9. The formulation according to any one of technical solutions 1-8, wherein said schizonepeta oil is the volatile oil extracted from the whole herb of fineleaf schizonepeta herb—*Schizonepeta tenuifolia* Briq of the Lamiaceae family.

10. The formulation according to any one of technical solutions 1-9, wherein said compounded volatile oils comprise, by volume, about 6 to 90% of eucalyptus oil, about 3 to 70% of forsythia oil, about 5 to 80% of clove oil, about 1 to 70% of patchouli oil, and about 1 to 85% of schizonepeta oil.

11. The formulation according to any one of technical solutions 1-10, wherein said compounded volatile oils comprise, by volume, about 21 to 71% of eucalyptus oil, about 8 to 48% of forsythia oil, about 15 to 60% of clove oil, about 3 to 47% of patchouli oil, and about 3 to 53% of schizonepeta oil, based on the total volume of said compounded volatile oils.

12. The formulation according to any one of technical solutions 1-11, wherein said compounded volatile oils comprise, by volume, about 18 to 63% of eucalyptus oil, about 5 to 19% of forsythia oil, about 6 to 27% of clove oil, about 6 to 16% of patchouli oil, and about 6 to 29% of schizonepeta oil, based on the total volume of said compounded volatile oils.

13. The formulation according to any one of technical solutions 1-12, wherein said compounded volatile oils comprise, by volume, about 43 to 52% of eucalyptus oil, about 13 to 20% of forsythia oil, about 21 to 30% of clove oil, about 7 to 15% of patchouli oil, and about 7 to 15% of schizonepeta oil.

14. The formulation according to any one of technical solutions 1-13, wherein said compounded volatile oils comprise, by volume, about 45% of eucalyptus oil, about 14% of forsythia oil, about 23% of clove oil, about 9% of patchouli oil, and about 9% of schizonepeta oil.

15. The formulation according to any one of technical solutions 1-14, wherein said compounded volatile oils comprise, by volume, eucalyptus oil:forsythia oil:clove oil:patchouli oil:schizonepeta oil of about 10:3:1:1:1.

16. The formulation according to any one of technical solutions 1-15, wherein said compounded volatile oils comprise, by volume, eucalyptus oil:forsythia oil:clove oil:patchouli oil:schizonepeta oil of about 15:4.5:7.5:3:7.

17. The formulation according to any one of technical solutions 3-16, wherein said vehicle is kerosene, isopropanol, absolute ethanol, or mixtures in any combination thereof.

18. The formulation according to technical solution 17, wherein said vehicle comprises, by volume, about 50 to 90% of kerosene, and about 10 to 50% of isopropanol or absolute ethanol, based on the total volume of said vehicle.

19. The formulation according to technical solution 17, wherein said vehicle comprises, by volume, about 71.4% of kerosene and about 28.6% of isopropanol or absolute ethanol.

20. The formulation according to any one of technical solutions 3-19, wherein said formulation is comprised of said compounded volatile oils and said vehicle.

21. The formulation according to technical solution 20, wherein said formulation comprises, by volume, about 1 to 100% of said compounded volatile oils and about 0 to 99% of said vehicle, based on the total volume of said formulation.

22. The formulation according to technical solution 20, wherein said formulation comprises, by volume, about 1 to 10% of said compounded volatile oils and about 90 to 99% of said vehicle, based on the total volume of said formulation.

23. The formulation according to technical solution 22, wherein said formulation comprises, by volume, about 2.5% of said compounded volatile oils and about 97.5% of said vehicle.

24. The formulation according to technical solution 22, wherein said formulation comprises, by volume, about 10% of said compounded volatile oils and about 90% of said vehicle.

25. Use of the formulation according to any one of technical solutions 1-24 in refreshing and disinfecting the air.

26. The use according to technical solution 25, wherein said formulation is dissipated into the air for filtering and cleansing the air, so as to achieve the objective of refreshing and disinfecting the air. 27. The use according to technical solution 25 or 26, wherein said formulation is dissipated into the air by means of heating and/or spraying.

28. A preparation process for the formulation according to any one of technical solutions 1-24, said process comprising the step of extracting said individual components of said compounded volatile oils.

29. The preparation process according to technical solution 28, said process comprising the following steps for extracting said individual components of said compounded volatile oils: extracting said individual components from the raw materials comprising said individual components using water-steam distillation, and/or extracting said individual components from the raw materials comprising said individual components using supercritical fluid extraction.

30. The preparation process according to technical solution 28 or 29, said process further comprising: separately measuring said individual components extracted, mixing them and optionally stirring to homogeneity, so as to obtain said compounded volatile oils.

31. The preparation process according to technical solution 30, said process further comprising the following steps: measuring said vehicle and optionally mixing said vehicle comprised of multi-components and then optionally stirring to homogeneity; and adding said vehicle into the mixture of said volatile oils and mixing them, optionally stirring the mixture of said volatile oils and said vehicle to homogeneity, so as to obtain said air-refreshing disinfectant formulation.

DETAILED DESCRIPTION OF THE INVENTION

As used herein, by "refreshing and disinfecting" is meant making the air have a natural fragrant scent and inhibiting and/or killing the bacteria and/or viruses commonly found in the air.

As used herein, "comprised of eucalyptus oil, clove oil, patchouli oil, forsythia oil and schizonepeta oil" is also referred to as compounded volatile oils, compounded traditional Chinese medicinal volatile oils or the like.

In the hereunder description of the preparation of the samples, the raw materials for the individual components of the compounded volatile oils are as follows:

Eucalyptus oil: General eucalyptus oil can be used. A specific example is the volatile oil extracted from bluegum—*Eucalyptus globulus* Labill of the Myrtaceae family or camphor tree—*Cinnamomum camphora* (L.) Presl of the Lauraceae family or other plants of the same genera to which the above two plants belong in the above two families. (The commercial product used in the Examples herein was purchased from Ganxu Perfume Oil Factory, Jishui County, Jiangxi Province, lot no. 20060825.)

Forsythia oil: General forsythia oil can be used. A specific example is the volatile oil extracted from the dried fruits of weeping forsythia—*Forsythia suspensa* (Thunb.) Vahl of the Oleaceae family. (The commercial product used in the Examples herein was purchased from Ganxu Perfume Oil Factory, Jishui County, Jiangxi Province, lot no. 20060825.)

Clove oil: General clove oil can be used. A specific example is the volatile oil extracted from the dried flower buds of clove—*Eugenia caryophyllata* Thunb. of the Myrtaceae family. (The commercial product used in the Examples herein was purchased from Ganxu Perfume Oil Factory, Jishui County, Jiangxi Province, lot no. 20060825.)

Patchouli oil: General patchouli oil can be used. A specific example is the volatile oil extracted from the dried stems and leaves of patchouli—*Pogostemon cablin* (Blanco) Benth of the Lamiaceae family. (The commercial product used in the Examples herein was purchased from Guangzhou Baihua Perfume Co., Ltd, Guangzhou, Guangdong Province, lot no. 20060901.) Schizonepeta oil: General schizonepeta oil can be used. A specific example is the volatile oil extracted from the whole herb of fineleaf schizonepeta herb—*Schizonepeta tenuifolia* Brig of the Lamiaceae family. (The commercial product schizonepeta oil used in the Examples herein was purchased from Ganxu Perfume Oil Factory, Jishui County, Jiangxi Province, lot no. 20060825.)

In addition to the commercially purchased products, the above-said volatile oils can be conventionally extracted from traditional Chinese medicinal materials using water steam distillation or supercritical fluid extraction or using other existing and known extraction methods.

The above-said eucalyptus oil, forsythia oil, clove oil, patchouli oil, and schizonepeta oil can also be respectively extracted from plants of other genera and other families.

Eucalyptus oil and patchouli oil were subjected to quality check as described under the relevant entries beginning at pages 280 and 272, respectively, in Part I of *Chinese Pharmacopoeia*, 2005 edition, clove oil was subjected to quality check as described in the entry beginning at page 7 in Part I of Chinese Pharmacopoeia, 1953 edition, and forsythia oil and schizonepeta oil were subjected to quality check using in-house developed standards.

Hereinunder described are the non-limiting examples of the present invention, wherein the composition of the formulations below is expressed in terms of volume, unless otherwise stated.

EXAMPLE 1

The bacteriostatic effects of individual and compounded traditional Chinese medicinal volatile oils (bacteriostatic ring method, Kirby-Bauer antibiotic testing, or disk dissusion antibiotic sensitivity testing).
Samples:
　Sample 1: eucalyptus oil
　Sample 2: forsythia oil
　Sample 3: patchouli oil
　Sample 4: clove oil
　Sample 5: Kirby-Bauer antibiotic testing, or disk dissusion antibiotic sensitivity testing) oil
　Sample 6: a mixture comprised of eucalyptus oil, forsythia oil, clove oil, patchouli oil and schizonepeta oil at a ratio of 10:3:1:1:1.

Method of preparation: 625.0 ml of eucalyptus oil, 187.5 ml of forsythia oil, 62.5 ml of clove oil, 62.5 ml of patchouli oil and 62.5 ml of schizonepeta oil were separately measured, mixed and stirred to homogeneity to obtain the mixture.
Experimental Strains:
*Staphylococcus aureus* (26112), *E. coli* (44113) and *Staphylococcus albus* (26069) were all provided by the National Institute for the Control of Pharmaceutical and Biological Products, Beijing, China.
Method of Assay:

The 16- to 18-hour liquid cultures of the above three strains were respectively spread on the surface of common culture plates evenly using sterile cotton swabs and the plates were allowed to dry briefly. Pieces of susceptibility paper with predetermined amount of respective sample solution absorbed in each piece were nipped with a sterile nipper and laid flat on the surface of the above plates which have been inoculated, with three pieces of susceptibility paper on each plate. Then the plates were incubated at 37° C. and observed the next day to obtain experimental results, as shown in Table 1.

TABLE 1

Experimental results of the bacteriostatic effects of individual traditional Chinese medicinal volatile oils (diameter of bacteriostatic ring, mm, n = 2 to 5, $\overline{X} \pm SD$)

| Sample | A (*Staphylococcus aureus*) | B (*Staphylococcus albus*) | C (*E. coli*) | D (Comprehensive bacteriostatic index) |
|---|---|---|---|---|
| 1 | 8.0 ± 1.1 | 12.5 ± 1.6 | 10.5 ± 0.5 | 10.2 |
| 2 | 8.3 ± 2.5 | 6.5 ± 0.5 | 8.3 ± 2.5 | 7.9 |
| 3 | 15.0 ± 0.0 | 9.0 ± 2.3 | 3.0 ± 3.3 | 7.8 |
| 4 | 30.0 ± 0.0 | 13.0 ± 0.0 | 6.0 ± 0.0 | 14.6 |
| 5 | 15.4 ± 0.5 | 9.5 ± 1.8 | 16.5 ± 6.1 | 14.8 |
| 6 | 20.3 ± 0.8 | 15.6 ± 2.6 | 11.6 ± 2.6 | 15.0 |

Note:
Comprehensive bacteriostatic index, D = A × 0.3 + B × 0.2 + C × 0.5 (the same applies below). n represents the number of repetitions of the experiment (the same applies below).

Results showed that eucalyptus oil, forsythia oil, patchouli oil, clove oil and schizonepeta oil had various degrees of inhibitory effect on the growth of *Staphylococcus aureus*,

*Staphylococcus albus* and *E. coli*. Clove oil had the strongest effect on *Staphylococcus aureus*, while schizonepeta oil had the strongest effect on *E. coli*.

Since three kinds of bacterial strains were used and the samples had various degrees of effect on different strains, it would be hard to evaluate the overall bacteriostatic effect of each of the samples simply by comparing the inhibitory effects of different samples on the three strains. Therefore, comprehensive evaluation was needed. In the present invention, the evaluation was made using the comprehensive index method.

The comprehensive index method is a commonly used comprehensive analysis method. Using this method, different weights were assigned to the bacteriostatic effects of each sample on the three strains, and the weighted bacteriostatic effects were simply added together to obtain a comprehensive bacteriostatic index for the sample (see the footnote of Table 1 for the formula of calculation). The assignment of weight was based on the importance of various factors and/or their contribution to the results. Here, coccus and *bacillus* represent two different categories of bacteria respectively and therefore both coccus and *bacillus* were assigned a weight of 0.5. Among the two coccal strains of used, *Staphylococcus aureus* was more pathogenic than *Staphylococcus* albus, therefore the two coccal strains were respectively assigned a weight of 0.3 and 0.2. Results showed that Sample 6 (compounded traditional Chinese medicinal volatile oils) had the highest comprehensive bacteriostatic index, indicating that the bacteriostatic effect of compounded traditional Chinese medicinal volatile oils was superior to that of the individual volatile oils. This suggested the reasonableness and superiority of the compounded formulation and reflected its novelty and inventiveness.

In order to further ascertain if the individual volatile oils had synergistic reinforcing effects after they were compounded, theoretic comprehensive bacteriostatic index was calculated based on the respective bacteriostatic effect of the individual volatile oils and the ratio of each of the individual volatile oils in Sample 6. The result obtained was 10.1, which was obviously lower than the actual comprehensive bacteriostatic index of 15.0 of Sample 6, suggesting that the individual volatile oils produced synergistic effect among themselves after they were compounded to form Sample 6 and thus enhanced the bacteriostatic effect. This confirmed the conclusion obtained from direct comparison of the determined comprehensive bacteriostatic indexes of the compounded formulation and the individual volatile oils, as described in the above paragraph, indicating the novelty and inventiveness of the compounded formulation.

EXAMPLE 2

The bacteriostatic effects of compounded traditional Chinese medicinal volatile oils having different ratios of individual volatile oils (bacteriostatic ring method, Kirby-Bauer antibiotic testing, or disk dissusion antibiotic sensitivity testing).

Samples:

Sample 7: a mixture comprised of eucalyptus oil, forsythia oil, clove oil, patchouli oil and schizonepeta oil at a ratio of 5:1.5:2.5:2:3.

Method of preparation: 357.1 ml of eucalyptus oil, 107.1 ml of forsythia oil, 178.6 ml of clove oil, 142.9 ml of patchouli oil and 214.3 ml of schizonepeta oil were separately measured, mixed and stirred to homogeneity to obtain the mixture.

Sample 8: a mixture comprised of eucalyptus oil, forsythia oil, clove oil, patchouli oil and schizonepeta oil at a ratio of 5:3:5:3:5.

Method of preparation: 238.1 ml of eucalyptus oil, 142.9 ml of forsythia oil, 238.1 ml of clove oil, 142.9 ml of patchouli oil and 238.1 ml of schizonepeta oil were separately measured, mixed and stirred to homogeneity to obtain the mixture.

Sample 9: a mixture comprised of eucalyptus oil, forsythia oil, clove oil, patchouli oil and schizonepeta oil at a ratio of 5:4.5:7.5:4:7.

Method of preparation: 178.6 ml of eucalyptus oil, 160.7 ml of forsythia oil, 267.9 ml of clove oil, 142.9 ml of patchouli oil and 250.0 ml of schizonepeta oil were separately measured, mixed and stirred to homogeneity to obtain the mixture.

Sample 10: a mixture comprised of eucalyptus oil, forsythia oil, clove oil, patchouli oil and schizonepeta oil at a ratio of 10:1.5:2.5:3:7.

Method of preparation: 416.7 ml of eucalyptus oil, 62.5 ml of forsythia oil, 104.2 ml of clove oil, 125.0 ml of patchouli oil and 291.7 ml of schizonepeta oil were separately measured, mixed and stirred to homogeneity to obtain the mixture.

Sample 11: a mixture comprised of eucalyptus oil, forsythia oil, clove oil, patchouli oil and schizonepeta oil at a ratio of 10:3:5:4:3.

Method of preparation: 400.0 ml of eucalyptus oil, 120.0 ml of forsythia oil, 200.0 ml of clove oil, 160.0 ml of patchouli oil and 120.0 ml of schizonepeta oil were separately measured, mixed and stirred to homogeneity to obtain the mixture.

Sample 12: a mixture comprised of eucalyptus oil, forsythia oil, clove oil, patchouli oil and schizonepeta oil at a ratio of 10:4.5:7.5:2:5.

Method of preparation: 344.8 ml of eucalyptus oil, 155.2 ml of forsythia oil, 258.6 ml of clove oil, 69.0 ml of patchouli oil and 172.4 ml of schizonepeta oil were separately measured, mixed and stirred to homogeneity to obtain the mixture.

Sample 13: a mixture comprised of eucalyptus oil, forsythia oil, clove oil, patchouli oil and schizonepeta oil at a ratio of 15:1.5:2.5:4:5.

Method of preparation: 535.7 ml of eucalyptus oil, 53.6 ml of forsythia oil, 89.3 ml of clove oil, 142.9 ml of patchouli oil and 178.6 ml of schizonepeta oil were separately measured, mixed and stirred to homogeneity to obtain the mixture.

Sample 14: a mixture comprised of eucalyptus oil, forsythia oil, clove oil, patchouli oil and schizonepeta oil at a ratio of 15:3:5:2:7.

Method of preparation: 468.8 ml of eucalyptus oil, 93.8 ml of forsythia oil, 156.3 ml of clove oil, 62.5 ml of patchouli oil and 218.8 ml of schizonepeta oil were separately measured, mixed and stirred to homogeneity to obtain the mixture.

Sample 15: a mixture comprised of eucalyptus oil, forsythia oil, clove oil, patchouli oil and schizonepeta oil at a ratio of 15:4.5:7.5:3:3.

Method of preparation: 454.5 ml of eucalyptus oil, 136.4 ml of forsythia oil, 227.3 ml of clove oil, 90.9 ml of patchouli oil and 90.9 ml of schizonepeta oil were separately measured, mixed and stirred to homogeneity to obtain the mixture.

The bacteriostatic effects of the above samples were determined by the method of Example 1. The experimental results are shown in Table 2.

TABLE 2

Experimental results of the bacteriostatic effects of compounded traditional Chinese medicinal volatile oils having different ratios of individual volatile oils (diameter of bacteriostatic ring, mm, n = 3, $\bar{X} \pm SD$)

| Sample | A (Staphylococcus aureus) | B (Staphylococcus albus) | C (E. coli) | D (Comprehensive bacteriostatic index) |
|---|---|---|---|---|
| 7 | 23.0 ± 1.0 | 7.7 ± 0.6 | 7.7 ± 0.6 | 12.3 |
| 8 | 25.3 ± 0.6 | 9.3 ± 0.6 | 7.3 ± 0.6 | 13.1 |
| 9 | 23.3 ± 0.6 | 9.3 ± 0.6 | 9.3 ± 0.6 | 13.5 |
| 10 | 25.0 ± 0.0 | 8.7 ± 0.6 | 9.7 ± 0.6 | 14.1 |
| 11 | 20.0 ± 0.0 | 8.3 ± 0.6 | 8.0 ± 0.0 | 11.7 |
| 12 | 20.3 ± 0.6 | 9.7 ± 0.6 | 8.7 ± 0.6 | 12.4 |
| 13 | 19.0 ± 1.0 | 8.3 ± 0.6 | 8.3 ± 0.6 | 11.5 |
| 14 | 18.0 ± 1.0 | 10.0 ± 1.0 | 9.3 ± 0.6 | 12.1 |
| 15 | 24.0 ± 1.0 | 9.3 ± 0.6 | 10.3 ± 0.6 | 14.2 |

(The ratios of each individual volatile oil in Samples 7 to 15 of this Example covered the following ranges: eucalyptus oil, 17.9 to 53.6%; forsythia oil, 5.4 to 16.1%; clove oil, 8.9 to 26.8%; patchouli oil, 6.3 to 16.0%; and schizonepeta oil, 9.1 to 29.2%.)

Results showed that the products of all the above nine formulations had bacteriostatic effect. The theoretic comprehensive bacteriostatic indexes for each of these formulations were calculated to be 11.4, 11.7, 11.8, 11.5, 10.9, 11.6, 10.9, 11.5 and 11.1 respectively, all lower than the corresponding determined comprehensive bacteriostatic indexes (column D, Table 2), which indicated that these nine formulations, through compounding, all produced synergistic effect in bacteriostatic action. Therefore the formulations of these nine samples also possessed novelty and inventiveness.

Among the nine formulations, Samples 7, 11, 12, 13 and 14 showed bacteriostatic effect, Samples 8, 9 and 10 showed good bacteriostatic effect, while Sample 15 showed the best bacteriostatic effect. Sample 15 comprised the individual volatile oils in the following ratios: eucalyptus oil, 45.5%; forsythia oil, 13.6%; clove oil, 22.7%; patchouli oil, 9.1%; and schizonepeta oil, 9.1%.

The above results were obtained from the experiments based on the orthogonal design $L_9$ ($3^4$) for different ratios of the individual volatile oils. Further analysis of the results according to the orthogonal design revealed that the change in the ratio of eucalyptus oil in the formulations did not affect the bacteriostatic effect very much; and the change in the ratios of forsythia oil, clove oil and schizonepeta oil affected the bacteriostatic effect considerably, with the bacteriostatic effect increasing with the increase in their ratios; while the ratio of patchouli oil affected the bacteriostatic effect the most, with the bacteriostatic effect first increasing and then decreasing at the ratio of patchouli oil from 6.3% to 16.0%. Based on the information acquired in this Example, the theoretical ratio of individual volatile oils resulting in the best bacteriostatic effect was 15:4.5:7.5:3:7, that is, eucalyptus oil, 40.5%; forsythia oil, 12.2%; clove oil, 20.3%; patchouli oil, 8.1%; and schizonepeta oil, 18.9%.

From this optimal ratio and the finding above that "the change in the ratio of eucalyptus oil in the formulations did not affect the bacteriostatic effect very much; and the change in the ratios of forsythia oil, clove oil and schizonepeta oil affected the bacteriostatic effect considerably, the bacteriostatic effect increasing with the increase in their ratios", it could be deduced that the ratios of individual volatile oils may vary in the following ranges: eucalyptus oil, 43 to 52%; forsythia oil, 13 to 20%; clove oil, 21 to 30%; patchouli oil, 7 to 15%; and schizonepeta oil, 7 to 15%; or alternatively, eucalyptus oil, 18 to 63%; forsythia oil, 5 to 19%; clove oil, 6 to 27%; patchouli oil, 6 to 16%; and schizonepeta oil, 6 to 29%; or alternatively, eucalyptus oil, 21 to 71%; forsythia oil, 8 to 48%; clove oil, 15 to 60%; patchouli oil, 3 to 47%; and schizonepeta oil, 3 to 53%; or alternatively, eucalyptus oil, 6 to 90%; forsythia oil, 3 to 70%; clove oil, 5 to 80%; patchouli oil, 1 to 70%; and schizonepeta oil, 1 to 85%.

Explanation on the Above-Said Ranges:

As the change in the ratio of eucalyptus oil in the formulations did not affect the bacteriostatic effect very much, the upper and lower limits of eucalyptus oil can vary widely. As to the change in the ratios of forsythia oil, clove oil and schizonepeta oil, besides the reasonable deduction made from the vicinity of their amounts in this Example, their upper limits may actually be higher than those in this Example, taking into consideration the fact that their bacteriostatic effects increased with the increase in their ratios.

Moreover, since the change in the viable amounts of the individual components in the formulations was continuous within a range, any combinations of the points disclosed in this Example and the endpoints as described above representing ranges are also viable, that is, they fall within the scope of the present invention as explicitly disclosed. Likewise, any matching of any range of amount of a component with any range of amount of any other component is also viable and is deemed to be part of the present invention as explicitly disclosed.

EXAMPLE 3

The bacteriostatic effects of compounded traditional Chinese medicinal volatile oils having different ratios of individual volatile oils (bacteriostatic ring method, Kirby-Bauer antibiotic testing, or disk diffusion antibiotic sensitivity testing).

Samples:

Sample 6: eucalyptus oil:forsythia oil:clove oil:patchouli oil:schizonepeta oil (10:3:1:1:1)

Method of preparation: 625.0 ml of eucalyptus oil, 187.5 ml of forsythia oil, 62.5 ml of clove oil, 62.5 ml of patchouli oil and 62.5 ml of schizonepeta oil were separately measured, mixed and stirred to homogeneity to obtain the mixture.

Sample 15: eucalyptus oil:forsythia oil:clove oil:patchouli oil:schizonepeta oil (15:4.5:7.5:3:3)

Method of preparation: 454.5 ml of eucalyptus oil, 136.4 ml of forsythia oil, 227.3 ml of clove oil, 90.9 ml of patchouli oil and 90.9 ml of schizonepeta oil were separately measured, mixed and stirred to homogeneity to obtain the mixture.

Sample 16: eucalyptus oil:forsythia oil:clove oil:patchouli oil:schizonepeta oil (15:4.5:7.5:3:7)

Method of preparation: 405.4 ml of eucalyptus oil, 121.6 ml of forsythia oil, 202.7 ml of clove oil, 81.1 ml of patchouli oil and 189.2 ml of schizonepeta oil were separately measured, mixed and stirred to homogeneity to obtain the mixture.

The bacteriostatic effects of the above samples were determined by the method of Example 1. The experimental results are shown in Table 3.

TABLE 3

Experimental results of the bacteriostatic effects of compounded traditional Chinese medicinal volatile oils having different ratios of individual volatile oils (diameter of bacteriostatic ring, mm, n = 3, $\overline{X} \pm SD$)

| Sample | A (Staphylococcus aureus) | B (Staphylococcus albus) | C (E. coli) | D (Comprehensive bacteriostatic index) |
|---|---|---|---|---|
| 6 | 20.0 ± 1.0 | 16.7 ± 3.2 | 9.7 ± 2.1 | 14.2 |
| 15 | 22.0 ± 1.0 | 10.0 ± 1.0 | 8.0 ± 1.0 | 12.6 |
| 16 | 24.0 ± 1.0 | 9.0 ± 1.0 | 10.7 ± 2.1 | 14.3 |

Results showed that the products of all the above three formulations had bacteriostatic effect. Sample 16 was the optimized formulation obtained by calculation based on the results of Example 2. The results in Table 3 showed that Sample 16 had good bacteriostatic effect. Its theoretic comprehensive bacteriostatic index was calculated to be 11.5, lower than its determined comprehensive bacteriostatic index of 14.3, which further demonstrated that the compounding produced synergistic effect that resulted in enhanced efficacy. The formulation of Sample 16 possessed novelty and inventiveness.

EXAMPLE 4

The bacteriostatic effects of compounded traditional Chinese medicinal volatile oils having different ratios of individual volatile oils (test tube dilution method)

Samples:

Sample 6: eucalyptus oil:forsythia oil:clove oil:patchouli oil:schizonepeta oil (10:3:1:1:1)

Method of preparation: 625.0 ml of eucalyptus oil, 187.5 ml of forsythia oil, 62.5 ml of clove oil, 62.5 ml of patchouli oil and 62.5 ml of schizonepeta oil were separately measured, mixed and stirred to homogeneity to obtain the mixture.

Sample 15: eucalyptus oil:forsythia oil:clove oil:patchouli oil:schizonepeta oil (15:4.5:7.5:3:3)

Method of preparation: 454.5 ml of eucalyptus oil, 136.4 ml of forsythia oil, 227.3 ml of clove oil, 90.9 ml of patchouli oil and 90.9 ml of schizonepeta oil were separately measured, mixed and stirred to homogeneity to obtain the mixture.

Sample 16: eucalyptus oil:forsythia oil:clove oil:patchouli oil:schizonepeta oil (15:4.5:7.5:3:7)

Method of preparation: 405.4 ml of eucalyptus oil, 121.6 ml of forsythia oil, 202.7 ml of clove oil, 81.1 ml of patchouli oil and 189.2 ml of schizonepeta oil were separately measured, mixed and stirred to homogeneity to obtain the mixture.

Experimental Method:

One ml of Tween 80 was added into 3 ml of each of Samples 6, 15 and 16 and allowed to dissolve. Then nutrient broth was added to obtain diluted samples of nine concentrations, i.e. 0.30 ml, 0.15 ml, 0.075 ml, 0.0375 ml, 0.01875 ml, 0.009375 ml, 0.004688 ml, 0.002344 ml or 0.001172 ml of crude drug per ml of the diluted sample, each tube having a total volume of 1 ml. Thermal sterilization was conducted.

Control tubes: strain control tube, having medium containing no drugs plus experimental strains; and drug control tube, having drug solution without experimental strains added.

For each row of drug solution, into each of the tubes having different concentrations and the strain control tube was added 0.1 ml of $10^6$ cfu·ml$^{-1}$ experimental strain solution (8-hour culture), and the tubes were incubated at 37° C. for 24 hours. From each of the tubes having different concentrations, a loop of sample was obtained using an inoculating loop and streak inoculated onto a solid nutrient agar plate. The plates were incubated at 37° C. for 24 hours, at which time the results were observed. Each tube was visually inspected for the growth of the strains with turbidity as the index, and each plate was visually inspected to see if there was growth of colonies.

The minimal inhibitory concentration (MIC) was determined, which refers to the lowest drug concentration required to completely inhibit the growth of the experimental strains.

The minimal bacteriocidal concentration (MBC) was determined, which refers to the lowest drug concentration required to completely kill the growth of the experimental strains.

The experimental results are shown in Table 4.

TABLE 4

Results of the determined MIC and MBC of compounded traditional Chinese medicinal volatile oils having different ratios of individual volatile oils for three bacterial strains (μl · ml$^{-1}$)

| Sample | Staphylococcus aureus | | Staphylococcus albus | | E. coli | | Comprehensive bacteriostatic index | |
|---|---|---|---|---|---|---|---|---|
| | A1 (MIC) | A2 (MBC) | B1 (MIC) | B2 (MBC) | C1 (MIC) | C2 (MBC) | D1 (MIC) | D2 (MBC) |
| 6 | 18.75 | 37.50 | 37.50 | 75.0 | 75.0 | 75.0 | 50.6 | 63.8 |
| 15 | 4.69 | 9.38 | 9.38 | 18.75 | 18.75 | 18.75 | 12.7 | 15.9 |
| 16 | 2.34 | 4.69 | 18.75 | 18.75 | 18.75 | 18.75 | 13.8 | 14.5 |

MIC and MBC are two important indexes representing the bacteriostatic and bacteriocidal effects of a drug. The lower the value, the better the effect of the drug against the bacteria. Using these two indexes, the bacteriostatic effects of Samples 6, 15 and 16 as a function of their concentrations were evaluated. Results showed that, the above three samples had various degrees of bacteriostatic and bacteriocidal effect on the experimental strains. The MIC for the strains was in the range of 2.34 μl·ml$^{-1}$ to 75.0 μl·ml$^{-1}$, and the MBC for the strains was in the range of 4.69 μl·ml$^{-1}$ to 75.0 μl·ml$^{-1}$. The comprehensive bacteriostatic and bacteriocidal indexes of MIC and MBC of Sample 16 were both the least, and the MIC of Sample 16 was close to that of Sample 15, indicating that Sample 16 had the best comprehensive bacteriostatic and bacteriocidal effects and also a good comprehensive bacteriostatic effect.

EXAMPLE 5

The antiviral effects of compounded traditional Chinese medicinal volatile oils having different ratios of individual volatile oils Samples:

Sample 6: eucalyptus oil:forsythia oil:clove oil:patchouli oil:schizonepeta oil (10:3:1:1:1)

Method of preparation: 625.0 ml of eucalyptus oil, 187.5 ml of forsythia oil, 62.5 ml of clove oil, 62.5 ml of patchouli oil and 62.5 ml of schizonepeta oil were separately measured, mixed and stirred to homogeneity to obtain the mixture.

Sample 15: eucalyptus oil:forsythia oil:clove oil:patchouli oil:schizonepeta oil (15:4.5:7.5:3:3)

Method of preparation: 454.5 ml of eucalyptus oil, 136.4 ml of forsythia oil, 227.3 ml of clove oil, 90.9 ml of patchouli oil and 90.9 ml of schizonepeta oil were separately measured, mixed and stirred to homogeneity to obtain the mixture.

Sample 16: eucalyptus oil:forsythia oil:clove oil:patchouli oil:schizonepeta oil (15:4.5:7.5:3:7)

Method of preparation: 405.4 ml of eucalyptus oil, 121.6 ml of forsythia oil, 202.7 ml of clove oil, 81.1 ml of patchouli oil and 189.2 ml of schizonepeta oil were separately measured, mixed and stirred to homogeneity to obtain the mixture.

Ribavirin (provided by Hubei Institute of Pharmaceutical Industry, Hubei, China; lot no. 0301006) was used as the positive drug control.

Viral Strain:

Influenza A virus FM 1 strain, provided by Institute of Medicinal Biotechnology, Chinese Academy of Medical Sciences, was passaged in MDCK cells (Madin-Darby Canine Kidney cells) which were incubated at 37° C. in a 5% $CO_2$ incubator. The viral titer was determined by cytopathic method and chicken erythrocyte agglutination method.

Experimental Method:

Viral experiment was performed in a 96-well microtiter plate (0.1 ml per well) according to *Guidelines for Research of New Drugs of Traditional Chinese Medicine* (promulgated by the Bureau of Drug Administration of the Ministry of Public Health of the People's Republic of China, 1994 edition). The cells were seeded in the wells at $1\times10^5$/ml and allowed to grow to monolayer. The drugs were diluted with maintenance solution into four different concentrations. Samples of the drugs at different concentrations were added to the wells at 0.1 ml/well after removing the original culturing solution from the wells. The minimal dilution at which the cells did not show pathological changes was taken as the limit of non-toxicity to the cells. At the same time, the $TCID_{50}$ (50% tissue culture infective dose) of the challenging virus was assayed on the MDCK cells. In the assay, virus control, cell control, drug toxicity control and positive drug control (ribavirin) were included. The cells were incubated at 37° C. in a 5% $CO_2$ incubator and observed for pathological changes under an inverted microscope every day, with the observations being recorded. When the cells in the virus control well showed +++ pathological changes, observation was continued for 7 days and then stopped. The degrees of cell pathological changes were recorded in the following 6-stage scale.—: cells grew normally, no pathological changes occurred; "±": cells with pathological changes were less than 10% of the whole cell monolayer; "+": cells with pathological changes were less than 25% of the whole cell monolayer; "++": cells with pathological changes were less than 50% of the whole cell monolayer; "+++": cells with pathological changes were less than 75% of the whole cell monolayer; and "++++". cells with pathological changes were more than 75% of the whole cell monolayer. The experimental results are shown in Table 5.

TABLE 5

The inhibitory effects of the samples of compounded traditional Chinese medicinal volatile oils having different ratios of individual volatile oils on influenza A virus FM1 strain

| Sample | FM1 infection dose ($TCID_{50}$) | Sublethal concentration of the drugs ($\mu l \cdot ml^{-1}$) | Inhibitory effect on the virus strain FM1 |
|---|---|---|---|
| 6 | 100 | 66 | — |
| 15 | 100 | 160 | + |
| 16 | 100 | 152 | — |
| Ribavirin | 100 | 100 | + |

Note:
"+": complete inhibition of the virus; "—": no inhibitory effect on the virus.

Results showed that, at an infection dose of the virus of $TCID_{50}=100$, 100 $\mu g \cdot ml^{-1}$ of ribavirin had markedly inhibitory effect on FM1, and 160 $\mu g \cdot ml^{-1}$ of Sample 15, which was at sublethal concentration, was also inhibitory. This indicated that Sample 15 also could inhibit the common virus in the air, therefore it had the effect of disinfecting the air. (In the examples that follow, the formulation of Sample 15 was chosen as subject of further research).

EXAMPLE 6

Simulated Field Experiment Sample:

Traditional Chinese medicinal air-refreshing disinfectant 1: prepared from compounded traditional Chinese medicinal volatile oils and a vehicle at a ratio of 1:9, wherein the compounded traditional Chinese medicinal volatile oils were comprised of eucalyptus oil, forsythia oil, clove oil, patchouli oil and schizonepeta oil at a ratio of 15:4.5:7.5:3:3, and the vehicle was comprised of kerosene and absolute ethanol at a ratio of 2.5:1.

Method of preparation: 45.5 ml of eucalyptus oil, 13.6 ml of forsythia oil, 22.7 ml of clove oil, 9.1 ml of patchouli oil and 9.1 ml of schizonepeta oil were separately measured, mixed and stirred to homogeneity to obtain compounded traditional Chinese medicinal volatile oils for immediate use. 642.9 ml of kerosene and 257.1 ml of absolute ethanol were separately measured, mixed and stirred to homogeneity, and then added to the above mixture of volatile oils. The resulting mixture was mixed and stirred to homogeneity to obtain the disinfectant 1.

MATERIALS AND EQUIPMENTS: Experimental strain: *Staphylococcus albus* 8032, provided by Academy of Military Medical Sciences, China. The strain was at the sixth to the eighth passages and was formulated into cell suspension using common broth.

Aerosol generator: more than 90% of the particles having $\Phi \leq 5$ $\mu m$.

Volume of the aerosol room: 10 $m^3$.

Sampler: FA-1 model impact type airborne microorganism sampler

Method:

Guidance for test: Item 2.1.3 in *Technical Standard For Disinfection*, 2002 edition, the Ministry of Public Health of China.

Test temperature: 23 to 24° C.; relative humidity: 50 to 58%.

The flow rate of sprayer for bacterial contamination: 21.7 L/min; spraying time: 5 min; stirring time: 5 min; standing time: 5 min.

Method of disinfection: When testing, the experimental chamber was sprayed using QPQ-2300 model electric aerosol sprayer at a dose of 2 $ml/m^3$ and samples were taken 60 minutes after disinfection. In the control group, deionized water was used in place of the disinfectant, and the other procedures were the same as the test group. The test was done in triplicate. Samples were taken using FA-1 model impact type airborne microorganism sampler at a sampling flow rate of 28.3 L/min. The sampling point was located 1.0 meter above the ground in the middle of the chamber.

Samples were taken at 0 min and at 60 min after disinfection. The sampling interval for the sampler of the control group was 5 second and 5 second respectively, and the sampling interval for the sampler of the test group was 5 second and 1 minute respectively. After sampling, the numbers of viable bacteria at different time points were determined and the killing rate was calculated according to the following formula:

$$N_t = \frac{V_0 - V_t}{V_0} \times 100\%$$

$$K_t = \frac{V_0'(1 - N_t) - V_t'}{V_0'(1 - N_t)} \times 100\%$$

$N_t$: natural death rate of the bacteria in the air;

$V_0$ and $V_t$: the numbers of bacteria contained in the air before the test and during the test respectively for the control group;

$K_t$: the killing rate of the bacteria in the air by disinfection;

$V_0'$ and $V_t'$: the numbers of bacteria contained in the air before disinfection and during disinfection respectively for the test group.

The results are shown in Table 6.

TABLE 6

The killing effect of traditional Chinese medicinal air-refreshing disinfectant 1 on *Staphylococcus albus*

| | | Control group | | Test group | |
|---|---|---|---|---|---|
| Test No. | Disinfection time (min) | Viable bacteria (cfu/m³) | Natural death rate (%) | Viable bacteria (cfu/m³) | Killing rate (%) |
| 1 | 0 | $3.08 \times 10^5$ | 0 | $3.21 \times 10^5$ | 0 |
| | 60 | $1.96 \times 10^5$ | 36.36 | $5.09 \times 10^3$ | 97.50 |
| 2 | 0 | $3.47 \times 10^5$ | 0 | $3.39 \times 10^5$ | 0 |
| | 60 | $2.23 \times 10^5$ | 33.14 | $8.38 \times 10^3$ | 96.30 |
| 3 | 0 | $3.74 \times 10^5$ | 0 | $3.49 \times 10^5$ | 0 |
| | 60 | $2.65 \times 10^5$ | 29.14 | $5.23 \times 10^3$ | 97.88 |

Negative control: No bacterial growth was seen in both the diluent and the media.

Results showed that 60 minutes of disinfection by traditional Chinese medicinal air-refreshing disinfectant 1 resulted in the killing of *Staphylococcus albus* at a killing rate of more than 96.30% in all three tests. This showed that traditional Chinese medicinal air-refreshing disinfectant 1 could kill the common bacteria in the air, therefore it had the bacteriocidal effect on the air.

EXAMPLE 7

Field Experiment

Samples:

Traditional Chinese medicinal air-refreshing disinfectant 2: prepared from compounded traditional Chinese medicinal volatile oils and a vehicle at a ratio of 1:39, wherein the compounded traditional Chinese medicinal volatile oils were comprised of eucalyptus oil, forsythia oil, clove oil, patchouli oil and schizonepeta oil at a ratio of 15:4.5:7.5:3:3, and the vehicle was comprised of kerosene and isopropanol at a ratio of 2.5:1.

Method of preparation: 11.4 ml of eucalyptus oil, 3.4 ml of forsythia oil, 5.7 ml of clove oil, 2.3 ml of patchouli oil and 2.3 ml of schizonepeta oil were separately measured, mixed and stirred to homogeneity to obtain compounded traditional Chinese medicinal volatile oils for immediate use. 642.9 ml of kerosene and 257.1 ml of isopropanol were separately measured, mixed and stirred to homogeneity, and then added to the above mixture of volatile oils. The resulting mixture was mixed and stirred to homogeneity to obtain the disinfectant 2.

Traditional Chinese medicinal air-refreshing disinfectant 3: prepared from compounded traditional Chinese medicinal volatile oils and a vehicle at a ratio of 1:9, wherein the compounded traditional Chinese medicinal volatile oils were comprised of eucalyptus oil, forsythia oil, clove oil, patchouli oil and schizonepeta oil at a ratio of 15:4.5:7.5:3:3, and the vehicle was comprised of kerosene and isopranol at a ratio of 2.5:1.

Method of preparation: 45.5 ml of eucalyptus oil, 13.6 ml of forsythia oil, 22.7 ml of clove oil, 9.1 ml of patchouli oil and 9.1 ml of schizonepeta oil were separately measured, mixed and stirred to homogeneity to obtain compounded traditional Chinese medicinal volatile oils for immediate use. 642.9 ml of kerosene and 257.1 ml of isopropanol were separately measured, mixed and stirred to homogeneity, and then added to the above mixture of volatile oils. The resulting mixture was mixed and stirred to homogeneity to obtain the disinfectant 3.

Experimental Environment and Equipment:

Room volume: 70 m³

Temperature and humidity: room temperature: 31° C., room relative humidity: 85%. Spraying equipment: electric aerosol sprayer, model DQP-600, available from Beijing Songyuan Huaxing Science and Technology Development Co., Ltd, Beijing, China.

Figure 1:
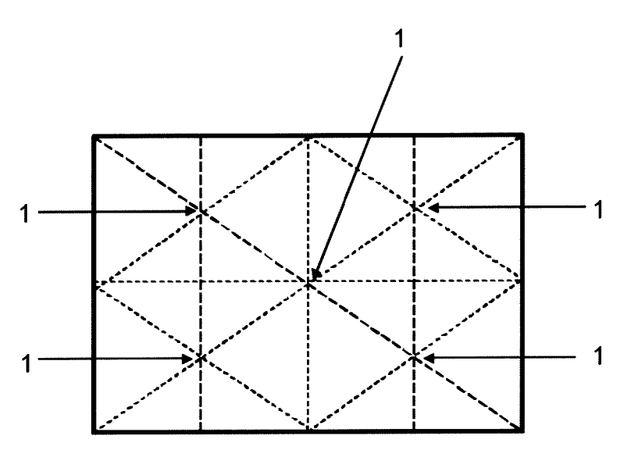
FIG. 1 is the plan view of the sampling points of the example of field experiment. Reference sign I represents the sampling points.

Disinfection and Sampling:

The sampling points are as shown in FIG. 1. A total of two samplings were made at 0 h and 2 h respectively.

Method of sampling: At each of the five sampling points as shown in FIG. 1, two plates having a diameter of 9 cm were placed at a sampling height of 1.0 m. The lids of the plates were removed and the plates were exposed to the air for 10 minutes. Then the plates were covered with the lids and incubated at 37° C. for 24 hours. The number of colonies was counted and the killing rate was calculated according to the following formula.

Killing rate =

$$\frac{-\text{Average No. of colonies from the sample after disinfection}}{\text{Average No. of colonies from the sample before disinfection}}$$

Disinfection operation: the disinfectant was sprayed evenly in the room using the electric aerosol sprayer at a dose of 1 ml/m³ and the room was allowed to be disinfected for 2 hours after spraying.

Statistical Test Method:

The results are shown in Tables 7 and 8.

TABLE 7

The disinfection effect of traditional Chinese medicinal air-refreshing disinfectant 2 in a closed room

| State of disinfection | Number of bacteria in the air (cfu/m$^3$) |
|---|---|
| Before disinfection | 529 |
| After disinfection | 152 |
| Killing rate | 71.3% |
| p | <0.01 |

TABLE 8

The disinfection effect of traditional Chinese medicinal air-refreshing disinfectant 3 in a closed room

| State of disinfection | Number of bacteria in the air (cfu/m$^3$) |
|---|---|
| Before disinfection | 608 |
| After disinfection | 147 |
| Killing rate | 75.9% |
| p | <0.01 |

Results showed that, disinfection of the air in a closed room using traditional Chinese medicinal air-refreshing disinfectants 2 and 3 resulted in a reduction in the number of bacteria in the air by about 71% and 76% respectively, which were statistically significant. This indicated that traditional Chinese medicinal air-refreshing disinfectants 2 and 3 could kill the bacteria in the air, therefore they had the bacteriocidal effect on the air.

In view of the data of "1:9" and "1:39" in this Example and the resulting effect, the ratio of the compounded volatile oils to the vehicle can vary in a wide range without appreciable influence on the effect. The present invention can be carried out in the following ranges:

Compounded volatile oils: >0 to ≤100%; vehicle: 0 to 99%; wherein ">0" means greater than 0.

Compounded volatile oils: 1 to 100%; vehicle: 0 to 99%; or Compounded volatile oils: 1 to 10%; vehicle: 90 to 99%.

There is no limitation on the selection of the vehicle that can be used, so long it serves to achieve the objective of the present invention. Such selection can be readily made by one skilled in the art through simple measurement. Examples of the vehicle include but not limited to kerosene, isopropanol, and absolute ethanol etc., or mixtures in any combination thereof.

EXAMPLE 8

Acute Oral Toxicity Test

Purpose of the Test:

To observe the toxicity response generated after administering the traditional Chinese medicinal air-refreshing disinfectant once to animals and to evaluate the safety of the air-refreshing disinfectant in human body during actual application in humans.

Sample:

Traditional Chinese medicinal air-refreshing disinfectant 2: prepared from compounded traditional Chinese medicinal volatile oils and a vehicle at a ratio of 1:39, wherein the compounded traditional Chinese medicinal volatile oils were comprised of eucalyptus oil, forsythia oil, clove oil, patchouli oil and schizonepeta oil at a ratio of 15:4.5:7.5:3:3, and the vehicle was comprised of kerosene and isopropanol at a ratio of 2.5:1.

Method of preparation: 11.4 ml of eucalyptus oil, 3.4 ml of forsythia oil, 5.7 ml of clove oil, 2.3 ml of patchouli oil and 2.3 ml of schizonepeta oil were separately measured, mixed and stirred to homogeneity to obtain compounded traditional Chinese medicinal volatile oils for immediate use. 696.4 ml of kerosene and 278.6 ml of isopropanol were separately measured, mixed and stirred to homogeneity, and then added to the above mixture of volatile oils. The resulting mixture was mixed and stirred to homogeneity to obtain the disinfectant 2.

The disinfectant 2 was diluted using Arawana® peanut oil (production date: Jan. 30, 2007) (other brands of peanut oil can be used of course) when the test was performed.

Test Animals:

NIH (National Institute of Health) mice (Certificate No.: 0027327), male:female=1:1, weight 18 to 22 g, provided by the Center for Experimental Animals of Guangdong Province, China.

Test Method:

Twenty NIH mice, male:female=1:1, weight 18 to 22 g, were subjected to adaptive feeding for 2 days. Prior to administration, the animals were fasted overnight, but with free access to water. For the test, 5.0287 g of traditional Chinese medicinal air-refreshing disinfectant 2 was diluted with a suitable amount of peanut oil to 20 ml. The animals were subjected to gastric perfusion once at a dose of 20 ml/kg of body weight, i.e., 5000 mg/kg of body weight, and immediately observed for their response. The animals were observed continually for two weeks, and the toxicity response and death distribution of the animals were recorded. The deceased animals were subjected to postmortem examination and the pathological changes recorded to determine if $LD_{50}$ was greater than 5000 mg/kg of body weight.

Results and Conclusion:

The results of the test showed that the animals receiving gastric perfusion with traditional Chinese medicinal air-refreshing disinfectant 2 once at a dose of 5000 mg/kg of body weight did not show appreciable toxicity response. The manifestations of the animals after administration were mainly decreased activities, with some animals being excited and jumping. Two hours after administration, the animals' activities basically returned to normal, with no occurrence of animal death. Therefore, the $LD_{50}$ for the animals was determined to be greater than 5000 mg/kg of body weight.

According to the following toxicity evaluation standards in *Technical Standard For Disinfection* (2002 Edition) issued by the Ministry of Public Health of China: $LD_{50}$ greater than 5000 mg/kg of body weight represents in fact no toxicity.

$LD_{50}$ in the range of 501 mg/kg to 5000 mg/kg of body weight represents low toxicity;

LD50 in the range of 51 mg/kg to 500 mg/kg of body weight represents medium toxicity;

LD50 in the range of 1 mg/kg to 50 mg/kg of body weight represents high toxicity; and LD50 less than 1 mg/kg of body weight represents extreme toxicity.

Since the traditional Chinese medicinal air-refreshing disinfectant 2 had an $LD_{50}$ of greater than 5000 mg/kg of body weight, it could be regarded as a non-toxic product.

CONCLUSIONS

The traditional Chinese medicinal air-refreshing disinfectant according to the present invention has marked bacteriostatic, bacteriocidal and even antiviral activity. Its formulation is novel and can significantly inhibit the growth of common pathogenic bacteria in the air. Oral administration of the disinfectant at a dose of 5000 mg/kg of body weight did not result in obvious toxicity response and occurrence of animal death, suggesting its safety and effectiveness. Its formulation, with a refreshing odor, can be used for disinfecting and refreshing the air.

All examples herein are all non-limiting examples. All numerical values cited can also be approximate values unless particularly specified. Any combinations of the points disclosed in the examples and the endpoints representing ranges also fall within the scope of the present invention. Any matching of any range of amount of a component with any range of amount of any other component is also deemed to be part of the present invention. Modifications made according to the present invention are also deemed to be part of the present invention.

What is claimed is:

1. An air-refreshing disinfectant formulation comprising volatile oils, wherein said volatile oils comprise, by volume, about 18% to about 63% of eucalyptus oil, about 5% to about 19% of forsythia oil, about 6% to about 27% of clove oil, about 6% to about 16% of patchouli oil, and about 6% to about 29% of schizonepeta oil, based on the total volume of said volatile oils.

2. The air-refreshing disinfectant formulation of claim 1, wherein said formulation further comprises a vehicle.

3. The air-refreshing disinfectant formulation of claim 1, wherein said eucalyptus oil is a volatile oil extracted from a plant of the *Eucalyptus* genus or a plant of the *Cinnamomum* genus.

4. The air-refreshing disinfectant formulation of claim 1, wherein said forsythia oil is a volatile oil extracted from a dried fruit of *Forsythia suspensa*.

5. The air-refreshing disinfectant formulation of claim 1, wherein said clove oil is a volatile oil extracted from a dried flower bud of *Eugenia caryophyllata*.

6. The air-refreshing disinfectant formulation of claim 1, wherein said patchouli oil is a volatile oil extracted from a dried stem and leaf of *Pogostemon cablin*.

7. The air-refreshing disinfectant formulation of claim 1, wherein said schizonepeta oil is a volatile oil extracted from a whole herb of *Schizonepeta tenuifolia*.

8. The air-refreshing disinfectant formulation of claim 1, wherein said volatile oils comprise, by volume, about 45% of eucalyptus oil, about 14% of forsythia oil, about 23% of clove oil, about 9% of patchouli oil, and about 9% of schizonepeta oil, based on the total volume of said volatile oils.

9. The air-refreshing disinfectant formulation of claim 1, wherein said volatile oils comprise, by volume, eucalyptus oil:forsythia oil:clove oil:patchouli oil:schizonepeta oil at a ratio of about 10:3:1:1:1.

10. The air-refreshing disinfectant formulation of claim 1, wherein said volatile oils comprise, by volume, eucalyptus oil:forsythia oil:clove oil:patchouli oil:schizonepeta oil at a ratio of about 15:4.5:7.5:3:7.

11. The air-refreshing disinfectant formulation of claim 2, wherein said vehicle is selected from the group consisting of kerosene, isopropanol, absolute ethanol, or mixtures in any combination thereof.

12. The air-refreshing disinfectant formulation of claim 11, wherein said vehicle comprises, by volume, about 50 to about 90% of kerosene, and about 10 to about 50% of isopropanol or absolute ethanol, or mixtures in any combination thereof, based on the total volume of said vehicle.

13. The air-refreshing disinfectant formulation of claim 11, wherein said vehicle comprises, by volume, about 71.4% of kerosene and about 28.6% of isopropanol or absolute ethanol, based on the total volume of said vehicle.

14. The air-refreshing disinfectant formulation of claim 2, wherein said formulation comprises, by volume, about 1 to about 100% of said volatile oils and about 0 to 99% of said vehicle, based on the total volume of said formulation.

15. The air-refreshing disinfectant formulation of claim 2, wherein said formulation comprises, by volume, about 1 to about 10% of said volatile oils and about 90 to 99% of said vehicle, based on the total volume of said formulation.

16. The air-refreshing disinfectant formulation of claim 15, wherein said formulation comprises, by volume, about 2.5% of said volatile oils and about 97.5% of said vehicle, based on the total volume of said formulation.

17. The air-refreshing disinfectant formulation of claim 15, wherein said formulation comprises, by volume, about 10% of said volatile oils and about 90% of said vehicle, based on the total volume of said formulation.

18. An air-refreshing disinfectant formulation, wherein said volatile oils comprise, by volume, about 43 to about 52% of eucalyptus oil, about 13 to about 20% of forsythia oil, about 21 to about 30% of clove oil, about 7 to about 15% of patchouli oil, and about 7 to about 15% of schizonepeta oil, based on the total volume of said volatile oils.

19. A method of refreshing and disinfecting air comprising the step of dissipating the formulation of claim 1 into the air.

20. A method of refreshing and disinfecting air comprising the step of filtering the air with the formulation of claim 1.

21. A method of refreshing and disinfecting air comprising the step of dissipating the formulation of claim 1 into the air by means of heating or spraying the formulation.

22. A process for preparing the formulation of claim 1, the process comprising the steps of:
 (a) extracting the volatile oils from raw materials, wherein the volatile oils comprise eucalyptus oil, forsythia oil, clove oil, patchouli oil and schizonepeta oil; and
 (b) mixing the volatile oils of step (a).

23. The process of claim 22, wherein step (a) is performed using water-steam distillation or supercritical fluid extraction.

24. The process of claim 22, wherein the volatile oils obtained in step (a) are separately measured, and wherein the process further comprising the step of:
 (c) optionally stirring the mixture obtained by step (b) to homogeneity.

25. The process of claim 24, wherein the process further comprises the steps of:
 (d) measuring one or more vehicles;
 (e) optionally mixing the vehicles of step (d);
 (f) optionally stirring the vehicles of step (e) to homogeneity;
 (g) adding the vehicles of step (d), step (e), or step (f) to the mixture obtained by step (b);
 (h) mixing the vehicles of step (d), step (e), or step (f) with the mixture obtained by step (b); and
 (i) optionally stirring the mixture obtained by step (h).

* * * * *